United States Patent [19]

Doe, Jr. et al.

[11] 4,202,782
[45] May 13, 1980

[54] MULTIFUNCTIONAL ADDITIVES FOR LUBRICANTS

[75] Inventors: Lester A. Doe, Jr., Newtown; Lester A. Brooks, Norwalk, both of Conn.

[73] Assignee: R. T. Vanderbilt Company, Inc., Norwalk, Conn.

[21] Appl. No.: 914,839

[22] Filed: Jun. 12, 1978

[51] Int. Cl.$^2$ ...................... C10M 1/32; C09K 15/20; C07C 85/18
[52] U.S. Cl. .................. 252/51.5 A; 252/50; 252/51.5 R; 252/390; 252/392; 252/401; 252/403; 260/576
[58] Field of Search ............... 252/50, 51.5 A, 51.5 R, 252/401, 390, 392; 260/576

[56] References Cited

U.S. PATENT DOCUMENTS

| | | | |
|---|---|---|---|
| 2,002,642 | 5/1935 | Meuser et al. | 260/130 |
| 2,037,932 | 4/1936 | Semon | 252/50 X |
| 2,160,223 | 5/1939 | Meuser et al. | 260/566 |
| 2,202,934 | 6/1940 | Tuley et al. | 260/65 |
| 2,233,590 | 3/1941 | Dewey | 260/65 |
| 2,662,815 | 12/1953 | Rudel | 252/51.5 R X |
| 3,219,704 | 11/1965 | Wilder et al. | 260/576 |
| 3,282,840 | 11/1966 | Foster et al. | 252/50 |
| 3,696,851 | 10/1972 | Randell | 252/51.5 A |
| 3,739,026 | 6/1973 | Wilson | 260/576 |
| 3,770,377 | 11/1973 | Scott et al. | 252/390 X |

OTHER PUBLICATIONS

Maeda et al., Chem. Abstracts, vol. 61, 13227h, 6/64 (Japan Pat. No. 11,363).
Cohen et al., Ind. and Eng. Chem., vol. 45, pp. 1766–1774, 8/53.

Primary Examiner—Andrew Metz
Attorney, Agent, or Firm—Rasma B. Balodis

[57] ABSTRACT

Condensation product is prepared by condensing diphenylamine and 2-octanone in the presence of acid catalyst. The product is formulated with p,p'-dioctyldiphenylamine antioxidant and incorporated in lubricants for inhibition of degradation due to oxidation and corrosion.

5 Claims, 1 Drawing Figure

MULTIFUNCTIONAL ADDITIVES FOR LUBRICANTS

BACKGROUND OF THE INVENTION

Lubricating oils and greases, and similar oleaginous materials are used under circumstances which contribute to their breakdown during normal service. The severe high temperature operating conditions of modern engines accelerate deterioration of lubricants due to oxidation. Oxidative deterioration is accompanied by formation of gum, sludge and acids which may cause metal corrosion as well as chemical breakdown of the lubricant. One of the principal targets of lubricant improvement is their anticorrosive properties with respect to other lubricant additives.

Additives performing as antioxidants, antiwear agents and dispersants are often corrosive themselves and/or break down during normal use into corrosive substances which result in severe corrosive attack on metals and premature replacement of machinery.

In the past, diphenylamines have been used as antioxidants and corrosion inhibitors for various lubricating compositions. Specifically, p,p'-dioctyl-diphenylamine has been used for such application either alone or in combination with other corrosion inhibitors to enhance its corrosion inhibiting properties towards certain metals, particularly copper.

It is known that condensation products of diphenylamine and ketone have been used as antioxidants in various lubricating compositions. However, the individual condensation products of diphenylamine and ketone do not perform satisfactorily at higher operating temperatures, especially in engines. Particularly unsatisfactory protection is obtained against the formation of acids and sludge. The prior art condensation products have been prepared by high temperature reaction methods, e.g. 200° C. which yield products of cyclic structure. It has now been discovered that the corrosion properties of the condensation products can be improved by conducting the condensation reaction at low temperature so that predominately linear condensation products are obtained.

SUMMARY OF THE INVENTION

According to the invention, oil-soluble condensation products the major portion of which has linear structure are prepared by condensing diphenylamine and 2-octanone in the molar ratio of about 1:1.6 in the presence of acid catalyst at reflux temperature with or without the use of alcoholic solvent.

According to another aspect of the invention, there are provided corrosion and oxidation inhibiting compositions comprising p,p'-dioctyldiphenylamine and condensation product of diphenylamine and 2-octanone wherein the ratio of the p,p'-dioctyldiphenylamine to the condensation product ranges from about 5:1 to 1:3 and preferably from about 1:1 to 1:3.

It is another object of the invention to provide lubricating compositions comprising of major portion of lubricating oil and about 1.5 to 2.0 parts per hundred parts of oil of a corrosion and oxidation inhibiting composition of the invention.

DETAILED DESCRIPTION OF THE INVENTION

Figure 1:
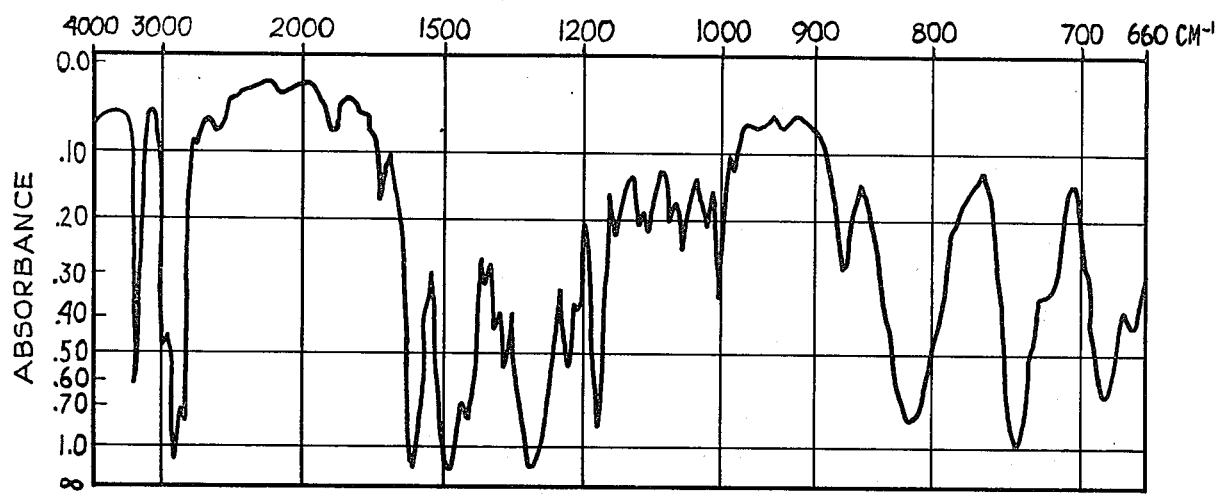

The condensation products of the invention are prepared by condensing diphenylamine and 2-octanone at reflux temperature and in the presence of an acid catalyst. Any acid condensation catalyst may be used. Preferred catalysts are hydrochloric acid, sulfuric acid, sulfonic acid such as chloro-, methane-, or p-toluenesulfonic acid and phosphoric acid.

The condensation may be conducted in the presence or absence of a solvent. The solvent may be selected from aliphatic alcohols. Preferred solvents are lower alkanols such as isopropanol and ethanol.

The oil-soluble condensation product consists primarily of compounds having a linear structure and a small amount of compounds having a cyclic structure.

FIG. 1 shows infrared absorption spectrum of a typical condensation product. The spectrum was obtained by using NaCl tablet.

According to the infrared spectrum, the linear components of the condensation product have a partial structure of the formula

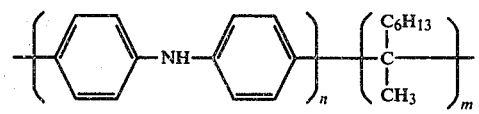

where n>m.

The cyclic minority components have basically a dihydro-9,10-acridine structure.

In general, condensation products of aromatic amine and ketone are composite complex substances of varying constitution. The specific composition and consequently properties will depend on the method of preparation.

Condensation at high temperature e.g. 200° C. yield cyclic structures while the condensation products of the invention are prepared under relatively low temperature conditions and yield compounds of linear structure. These linear products are soluble in oil and thus, are suitable for application in various oleagineous media.

The product exhibits particularly good corrosion inhibiting properties especially towards copper. It is compatible with aromatic amine type antioxidants and can be used in formulation of multifunctional lubricant additives.

It is particularly advantageous to combine the condensation product of diphenylamine and 2-octanone with p,p'-dioctyldiphenylamine. The latter exhibits good antioxidant properties and corrosion inhibiting properties toward metals with the exception of copper. Therefore, for complete oxidation and corrosion protection, it must be admixed with a compatible corrosion inhibitor.

Good overall protection of lubricants is obtained using compositions containing p,p'-dioctyldiphenylamine and the condensation product in the ratio ranging from about 5:1 to 1:3 and preferably from about 1:1 to 1:3. The multifunctional composition is incorporated into the lubricant by common techniques in the amount of about 1.5 to 2.0 parts per 100 parts lubricant.

The composition of the invention can be used for protection against oxidation and corrosion of variety of oleaginous materials: oils of lubricating viscosity such as hydrocarbon, mineral, naphthenic, paraffinic and synthetic oils of the ester, alkylene oxide, alkylene and silicone type, hydraulic fluids, crankcase oils, and transmission fluids.

EXAMPLE 1

Diphenylamine 676 g (4.00 moles), 2-octanone 817 g (6.40 moles) and concentrated hydrochloric acid 58 ml (0.70 moles) were added to the reaction flask. The reaction mixture was heated to reflux and aqueous HCl and 2-octanone mixture was azeotropically distilled until the reaction temperature reached about 165° C. After cooling to 150°–155° C., the azeotrope was slowly poured back into the reactor. As a result, the reaction temperature was lowered to 108° C. The procedure was repeated until nearly constant volume of aqueous hydrochloric acid was obtained (98 ml).

After cooling the reaction mixture to 90° C., hydrochloric acid was neutralized by slowly adding 37.6 g (0.355 moles) sodium carbonate with minimum foaming. Any unreacted 2-octanone was removed by steam distillation. The reaction product was dissolved in benzene, washed with water and dried to give 1009 g of brown viscous liquid. The condensation products have a predominantly linear structure as indicated by the infrared absorbance spectrum (NaCl tablet) in FIG. 1. The product is characterized by NH stretch at a frequency of 3340 cm$^{-1}$ and a strong peak at 810 to 820 cm$^{-1}$ which indicates a substitution at 4,4'-position of the phenyl ring and consequently a linear condensation product.

A smaller peak at 720 to 740 cm$^{-1}$ indicates a small amount of 2,2'- substitution on the benzene ring resulting from a cyclic or 9,10-dihydroacridine structure. This is partially masked by the diphenylamine band at 735 to 750 cm$^{-1}$.

EXAMPLE 2

The condensation product described in Example 1 was combined with various amounts of p,p'-dioctyldiphenylamine antioxidant and incorporated into synthetic ester lubricant (Hercolube A manufactured by Hercules Inc.)

The samples were subjected to a catalytic oxidation test for lubricants by the MIL-L-7808 Oxidation Test Method. Oxygen was bubbled through the samples at a rate of 5 l/hr for 72 hours at 218° C. The additives were rated on the basis of oil deterioration prevention as measured by (1) the increase in acid formation or neutralization number, (2) increase in Kinematic viscosity and (3) degree of metal corrosion. The data in Table I below indicates that the combination of p,p'-dioctyldiphenylamine and condensation product of diphenylamine and 2-octanone provide satisfactory protection against deterioration due to corrosion as well as oxidation. The corrosion of all metals tested is very low (<0.3 mg/cm$^2$). There is only slight increase in the neutralization number and acceptable increase in viscosity. No sludge was formed.

The components tested separately gave inadequate protection against deterioration of the lubricating oil. The known oxidation and corrosion inhibitor phenyl-β-naphthylamine in combination with p,p'-dioctyldiphenylamine is used as standard.

TABLE I

| Additive | Content, parts per 100 parts lubricant | | | | | |
|---|---|---|---|---|---|---|
| | 1 | 2 | 3 | 4 | 5 | 6 |
| Phenyl-β-naphthylamine | | | | | | 0.75 |
| p,p'-Dioctyldiphenylamine | 1.50 | — | 1.25 | 0.75 | 0.50 | 0.75 |
| Condensation product | — | 1.50 | 0.25 | 0.75 | 1.50 | — |
| Total | 1.50 | 1.50 | 1.50 | 1.50 | 2.00 | 1.50 |
| Test Results | | | | | | |
| Viscosity, percent increase | 40.7 | 13.9 | 20.6 | 33.2 | 28.5 | 17.4 |
| Neutralization number, increase | 3.26 | 5.65 | 1.86 | 2.61 | 1.96 | 2.49 |
| Sludge formation | none | moderate | none | none | none | slight |
| Metal corrosion, Weight change mg/cm$^2$ | | | | | | |
| Al | −0.02 | +0.01 | −0.08 | +0.01 | +0.01 | −0.02 |
| Cu | −1.49 | −0.23 | −0.33 | −0.22 | −0.21 | −0.35 |
| Mg | −0.01 | −0.09 | −0.08 | +0.03 | +0.04 | −0.17 |
| Fe | −0.02 | +0.04 | −0.03 | +0.02 | +0.02 | −0.04 |
| Ag | −0.03 | +0.06 | −0.05 | +0.02 | −0.01 | −0.05 |

What is claimed is:

1. An oil soluble condensation product characterized by having a predominantly linear structure and prepared by reacting diphenylamine and 2-octanone in the molar ratio of about 1:1.6 at reflux temperature in the presence of acid condensation catalyst.

2. A condensation product according to claim 1 wherein diphenylamine and 2-octanone are reacted in alcoholic media.

3. A corrosion and oxidation inhibiting composition comprising about 5 to 1 parts by weight p,p'-dioctyldiphenylamine and about 1 to 3 parts by weight condensation product characterized by having a predominantly linear structure and prepared by reacting diphenylamine and 2-octanone in the molar ratio of about 1:1.6 at reflux temperature and in the presence of acid condensation catalyst.

4. A lubricating composition comprising a major portion of oil of lubricating viscosity and about 1.5 to 2.0 parts by weight per hundred parts oil of a corrosion and oxidation inhibiting composition comprising about 5 to 1 parts by weight p,p'-dioctyldiphenylamine and about 1 to 3 parts by weight condensation product characterized by having a predominantly linear structure and prepared by reacting diphenylamine and 2-octanone in the molar ratio of about 1:1.6 at reflux temperature and in the presence of acid condensation catalyst.

5. A lubricating composition according to claim 4 wherein the corrosion and oxidation inhibiting composition comprises 1 part by weight p,p'-dioctyldiphenylamine and 1 part by weight condensation product and is present in an amount of 1.5 parts per 100 parts lubricant.

* * * * *